United States Patent
Kung et al.

(10) Patent No.: US 9,752,176 B2
(45) Date of Patent: Sep. 5, 2017

(54) METHODS FOR PREPARATIVE IN VITRO CLONING

(75) Inventors: Li-yun A. Kung, Arlington, MA (US); Daniel Schindler, Newton, MA (US); Joseph Jacobson, Newton, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 13/524,164

(22) Filed: Jun. 15, 2012

(65) Prior Publication Data

US 2012/0322681 A1   Dec. 20, 2012

Related U.S. Application Data (60) Provisional application No. 61/497,506, filed on Jun. 15, 2011.

(51) Int. Cl.
*C12Q 1/68* (2006.01)

(52) U.S. Cl.
CPC ......... *C12Q 1/6806* (2013.01); *C12Q 1/6855* (2013.01); *C12Q 2525/191* (2013.01); *C12Q 2533/107* (2013.01)

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. | |
| 5,288,514 A | 2/1994 | Ellman | |
| 5,384,261 A | 1/1995 | Winkler et al. | |
| 5,510,270 A | 4/1996 | Fodor et al. | |
| 5,514,789 A | 5/1996 | Kempe | |
| 5,527,681 A | 6/1996 | Holmes | |
| 5,541,061 A | 7/1996 | Fodor et al. | |
| 5,604,097 A | 2/1997 | Brenner | |
| 5,639,603 A | 6/1997 | Dower et al. | |
| 5,700,637 A | 12/1997 | Southern | |
| 5,700,642 A | 12/1997 | Monforte et al. | |
| 5,738,829 A | 4/1998 | Kempe | |
| 5,739,386 A | 4/1998 | Holmes | |
| 5,770,358 A | 6/1998 | Dower et al. | |
| 5,830,655 A | 11/1998 | Monforte | |
| 6,042,211 A | 3/2000 | Hudson et al. | |
| 6,248,521 B1 | 6/2001 | Van Ness et al. | |
| 6,375,903 B1 | 4/2002 | Cerrina et al. | |
| 6,416,164 B1 | 7/2002 | Stearns et al. | |
| 6,432,360 B1 | 8/2002 | Church | |
| 6,511,849 B1 | 1/2003 | Wang | |
| 6,514,704 B2 | 2/2003 | Bruce et al. | |
| 6,596,239 B2 | 7/2003 | Williams et al. | |
| 6,658,802 B2 | 12/2003 | Lucas, Jr. et al. | |
| 6,664,388 B2 | 12/2003 | Nelson | |
| 6,800,439 B1 | 10/2004 | McGall et al. | |
| 6,802,593 B2 | 10/2004 | Ellson et al. | |
| 6,824,866 B1 | 11/2004 | Glazer et al. | |
| 6,830,890 B2 | 12/2004 | Lockhart et al. | |
| 6,833,450 B1 | 12/2004 | McGall et al. | |
| 6,911,132 B2 | 6/2005 | Pamula et al. | |
| 6,932,097 B2 | 8/2005 | Ellson et al. | |
| 7,090,333 B2 | 8/2006 | Mutz et al. | |
| 7,133,782 B2 | 11/2006 | Odedra | |
| 7,169,560 B2 | 1/2007 | Lapidus et al. | |
| 7,323,320 B2 | 1/2008 | Oleinikov | |
| 7,563,600 B2 | 7/2009 | Oleinikov | |
| 8,053,191 B2 | 11/2011 | Blake | |
| 8,716,467 B2 | 5/2014 | Jacobson | |
| 8,808,986 B2 | 8/2014 | Jacobson et al. | |
| 2001/0012537 A1 | 8/2001 | Anderson et al. | |
| 2001/0053519 A1 | 12/2001 | Fodor et al. | |
| 2002/0037579 A1 | 3/2002 | Ellson et al. | |
| 2002/0081582 A1 | 6/2002 | Gao et al. | |
| 2003/0047688 A1 | 3/2003 | Faris et al. | |
| 2003/0068633 A1 | 4/2003 | Belshaw et al. | |
| 2003/0171325 A1 | 9/2003 | Gascoyne et al. | |
| 2003/0186226 A1 | 10/2003 | Brennan et al. | |
| 2003/0215837 A1 | 11/2003 | Frey | |
| 2004/0009479 A1 | 1/2004 | Wohlgemuth et al. | |
| 2004/0101894 A1 | 5/2004 | Albert et al. | |
| 2004/0106728 A1 | 6/2004 | McGall et al. | |
| 2004/0185484 A1 | 9/2004 | Costa et al. | |
| 2005/0079510 A1 | 4/2005 | Berka et al. | |
| 2005/0202429 A1 | 9/2005 | Trau et al. | |
| 2005/0227235 A1 | 10/2005 | Carr et al. | |
| 2006/0035218 A1 | 2/2006 | Oleinikov | |
| 2006/0040297 A1 | 2/2006 | Leamon et al. | |
| 2006/0054503 A1 | 3/2006 | Pamula et al. | |
| 2006/0127926 A1 | 6/2006 | Belshaw et al. | |
| 2007/0122817 A1* | 5/2007 | Church ................ C12Q 1/6806 435/6.16 |
| 2007/0281309 A1 | 12/2007 | Kong et al. | |

(Continued)

FOREIGN PATENT DOCUMENTS

| EP | 1205548 | 5/2002 |
|---|---|---|
| EP | 2017356 | 12/2011 |

(Continued)

OTHER PUBLICATIONS

Margulies et al. Nature. 437: 376-380(2005).*
Margulies et al. Nature. 437 (2005) Supplemental materials (3) p. 1-34.*
Ramachandran et al. Journal of Virological Methods, vol. 151, Issue 2, Aug. 2008, pp. 217-224.*
Yehezkel et al. (De novo DNA synthesis using single molecule PCR, Nucleic Acids Research, 2008, vol. 36, No. 17, e107, Published online Jul. 30, 2008).*
Matzas et al. (High-fidelity gene synthesis by retrieval of sequence-verified DNA identified using high-throughput pyrosequencing, Nature Biotechnology 28, 1291-1294 (2010), Published online Nov. 28, 2010).*
Kosuri et al. (Scalable gene synthesis by selective amplification of DNA pools from high-fidelity microchips, Nature Biotechnology 28, 1295-1299 (2010), Published online Nov. 28, 2010).*

(Continued)

*Primary Examiner* — Aaron Priest
(74) *Attorney, Agent, or Firm* — Greenberg Traurig, LLP; Fang Xie (57) ABSTRACT

Methods and devices relate to the isolation of nucleic acids of interest from within a population of nucleic acids such as libraries of nucleic acid sequences.

25 Claims, 3 Drawing Sheets

(56) References Cited

U.S. PATENT DOCUMENTS

| | | | |
|---|---|---|---|
| 2008/0003571 A1 | 1/2008 | McKernan et al. | |
| 2008/0105829 A1 | 5/2008 | Faris | |
| 2009/0087840 A1 | 4/2009 | Baynes et al. | |
| 2009/0093378 A1 | 4/2009 | Bignell et al. | |
| 2009/0280497 A1* | 11/2009 | Woudenberg et al. | 435/6 |
| 2009/0280697 A1 | 11/2009 | Li et al. | |
| 2010/0015614 A1 | 1/2010 | Beer et al. | |
| 2010/0015668 A1 | 1/2010 | Staehler et al. | |
| 2010/0028873 A1* | 2/2010 | Belouchi et al. | 435/6 |
| 2010/0273219 A1 | 10/2010 | May et al. | |
| 2011/0160078 A1* | 6/2011 | Fodor et al. | 506/9 |
| 2012/0028843 A1 | 2/2012 | Ramu | |
| 2012/0220497 A1 | 8/2012 | Jacobson | |
| 2012/0283110 A1* | 11/2012 | Shendure | C40B 20/04 506/4 |
| 2012/0315670 A1 | 12/2012 | Jacobson | |
| 2013/0059296 A1 | 3/2013 | Jacobson et al. | |
| 2013/0059761 A1 | 3/2013 | Jacobson | |
| 2013/0224729 A1 | 8/2013 | Church et al. | |
| 2013/0225421 A1* | 8/2013 | Li | C12Q 1/6846 506/2 |
| 2013/0281308 A1 | 10/2013 | Jacobson | |
| 2013/0296192 A1 | 11/2013 | Jacobson | |
| 2013/0296194 A1 | 11/2013 | Jacobson | |
| 2013/0309725 A1 | 11/2013 | Jacobson | |

FOREIGN PATENT DOCUMENTS

| | | |
|---|---|---|
| WO | 9000626 | 1/1990 |
| WO | 9320092 | 10/1993 |
| WO | WO 99/42813 | 8/1999 |
| WO | 0188173 | 11/2001 |
| WO | WO 02/24597 | 3/2002 |
| WO | WO 03/040410 | 5/2003 |
| WO | WO 03/046223 | 6/2003 |
| WO | 03054232 | 7/2003 |
| WO | WO 03/064026 | 8/2003 |
| WO | WO 03/064027 | 8/2003 |
| WO | WO 03/064699 | 8/2003 |
| WO | WO 03/065038 | 8/2003 |
| WO | WO 03/066212 | 8/2003 |
| WO | WO 03/100012 | 12/2003 |
| WO | 2004024886 | 3/2004 |
| WO | WO 2004/029586 | 4/2004 |
| WO | WO 2004/031351 | 4/2004 |
| WO | WO 2004/031399 | 4/2004 |
| WO | 2004090170 | 10/2004 |
| WO | 2005059096 | 6/2005 |
| WO | 2005071077 | 8/2005 |
| WO | 2006031745 | 3/2006 |
| WO | 2006044956 | 4/2006 |
| WO | 2006076679 | 7/2006 |
| WO | 2006086209 | 8/2006 |
| WO | 2007136736 | 11/2007 |
| WO | 2008024319 | 2/2008 |
| WO | 2010025310 | 3/2010 |
| WO | WO2010025310 | * 4/2010 |
| WO | 2010115100 | 10/2010 |
| WO | WO2010115100 | * 10/2010 |
| WO | 2011066185 | 6/2011 |
| WO | 2011066186 | 6/2011 |
| WO | 2011056872 | 11/2011 |
| WO | 2013163263 | 10/2013 |
| WO | 2014004393 | 1/2014 |
| WO | 2014160004 | 10/2014 |
| WO | 2014160059 | 10/2014 |

OTHER PUBLICATIONS

Tian et al. (Accurate multiplex gene synthesis from programmable DNA microchips, Nature 432, 1050-1054 (Dec. 23, 2004)).*
White et al. (Digital PCR provides sensitive and absolute calibration for high throughput sequencing, BMC Genomics, 2009, 10:116, Published: Mar. 19, 2009).*
Blanchard, Alan P., "Synthetic DNA Arrays in Genetic Engineering," Plenum Press. 20: 111-123 (1998).
Duggan et al., "Expression Profiling Using cDNA Microarrays," Nat. Genet. S21:10-14 (1999).
McClain et al., "Genome Sequence Analysis of Helicobacter Pylori Strains Associated with Gastric Ulceration and Gastric Cancer," BMC Genomics, Biomed Central Ltd, London, IK. 10(1):3 (2009).
Margulies et al., "Genome Sequencing in Microfabricated High-Density Picolitre Reactors," Nature. 437: 376-380 (2005).
McGall et al., "Light-Directed Synthesis of High-Density Oligonucleotide Arrays Using Semiconductor Photoresists," Pro. Natl. Acad. Sci. 93(24):13555-13560 (1996).
Mitra et al., "Fluorescent in situ Sequencing on Polymerase Colonies," Analytical Biochemistry. 320:55-65 (2003).
Petrik et al., "Advances in Transfusion Medicine in the First Decade of the 21$^{st}$ Century: Advances in Miniaturized Technologies," Transfusion and Apheresis Science. 45(1): 45-51 (2011).
Ramachandran et al., "End-Point Limiting-Dilution Real-Time PCR Assay for Evaluation of Hepatitis C Virus Quasispecies in Serum: Performance Under Optimal and Suboptimal Conditions," Journal of Virological Methods. 151(2): 217-224 (2008).
Shendure et al., "Accurate Multiplex Polony Sequencing of an Evolved Bacterial Genome," Science. 309:1728-1732 (2005).
Stekel, D., "Microarrays: Making Them and Using Them," Microarray Bioinformatics. Cambridge University Press. pp. 211-230 (2003).
Vogelstein et al., "Digital PCR," Pro. Natl. Acad. Sci. 96(16):9236-9241 (1999).
Communication Relating to the Results of the Partial International Search for International Patent Application PCT/US2012/042597 mailed on Jun. 14, 2012.
International Search Report for International Patent Application PCT/US2012/042597 mailed on Nov. 30, 2012.
McCaughan, Frank et al., "Single-Molecule Genomics", The Journal of Pathology, 220: 297-306, (Jan. 1, 2009).
European Search Report issued in European Application No. 12735365.4 mailed Jul. 22, 2016.
Adessi et al., "Solid phase DNA amplification: characterisation of primer attachment and amplification mechanisms," Nucleic Acids Research, 28(20):E87, (Oct. 15, 2000).
Ashkin, A., "Applications of laser radiation pressure" Science, 210(4474): 1081-1088, (Dec. 5, 1980).
Aslanzadeh, "Brief Review: Preventing PCR Amplification Carry-over Contamination in a Clinical Laboratory". Annals of Clinical & Laboratory Science 34(4) :389 (2004).
Beer, N., et al., "On-chip, real time single-copy polymerase chain reaction in picoliter droplets," Analytical Chemistry, 79(22):8471-8475, (Nov. 15, 2007).
Bennett, S., "Solexa Ltd.," Pharmacogenomics, 5(4):433-8, (Jun. 2004).
Binkowski B. F. et al. "Correcting erros in synthetic DNA through consensus shuffling" Nucl. Acids Res., vol. 33, No. 6, e55, 2005.
Boal, J., et al. "Cleavage of oligodeoxyribonucleotides from controlled-pore glass supports and their rapid deprotection by gaseous amines," NAR, 24(15):3115-3117, (1996).
Cho, S., et al. "Creating, transporting, cutting and merging liquid droplets by electrowetting-based actuation for digital microfluidic circuits," J. of Microelectromechanical Systems, 12(1):70-80, (Feb. 2003).
Ellson, Picoliter: Ennabling Precise Transfer of Nanoliter and Picoliter Volumes. Drug Discovery Today 7(5 Suppl.) :s32 (2002).
Fidalgo, L., et al., "Surface induced froplet fusion in microfluidic devices," Lab on Chip, 7(8)984-986, (2007).
Fodor, S., et al., "Light-directed, spatially addressable parallel chemical synthesis," Science, 251(4995):767-773, (Feb. 15, 1991).
Greenberg, M. and Gilmore, J., "Cleavage of oligonucleotides from solid-phase support using o-nitrobenzyl photochemistry," J. of Org. Chem., 59(4):746-753, (Feb. 1994).
Grifith, E. and Aklella, S. "Coordinating Multiple Droplets in Planar Array Digital Microfluidic Systems," The International Journal of Robotics Research, 24(11):933-949, (Nov. 2005).

(56) References Cited

OTHER PUBLICATIONS

Gulati S. et al. "Opportunities for microfluidic technologies in synthetic biology." Journal of the Royal Society, vol. 6, Suppl. 4, pp. S493-S506, (2009).
Haeberle, S. and Zengerle, R., "Microfluidic platforms for lab-on-chip applications," Lab on a Chip 7(9):1094-1110, (2007).
Hardy, P., et al., "Reagents for the preparation of two oligonucleotides per synthesis (TOPSTM)," Nucleic Acids Research, 22(15):2998-3004, (1994).
Holmes, C., "Model studies for new o-nitrobenzyl photolabile linkers: substituent effects on the rates of photochemical cleavage," J. of Org. Chem., 62(8):2370-2380, (Apr. 18, 1997).
Hyman, E., "A new method of sequencing DNA," Analytical Biochemistry, 174(2):423-436, (Nov. 1, 1988).
Kahl, J., et al. "Solution-Phase Bioconjugate Synthesis Using Protected Oligonucleotides Containing 3'-Alkyl Carboxylic Acids," J. of Org. Chem., 64(2):507-510, (1999).
Kahl, J., et al., "High-Yielding Method for On-Column Derivatization of Protected Oligodeoxy-nucleotides and Its Application to the Convergent Synthesis of 5',3'-Bis-conjugates," J. of Org. Chem., 63(15):4870-.
Kelly, B., et al., "Miniaturizing chemistry and biology in microdroplets," Chem. Commun., 1773-1788, (2007).
Kong, D., et al., "Parallel gene synthesis in microfluidic device," Nucleic Acids Research, vol. 35, No. 8, pp. e61-1 (9 pages), (2007).
Lashkari et al. "An automated multiplex oligonucleotide synthesizer: Development of high throughput, low cost DNA synthesis". PNAS 92(17): 7912-7915, (1995).
Leamon, J., et al., "A massively parallel PicoTiterPlate™based platform for discrete picoliter-scale polymerase chain reactions," Electrophoresis, 24(21):3769-3777, (Nov. 2003).
Liu, Y., et al., "DNA ligation of ultramicrovolume using EWOD microfluidic system with coplanar electrodes: DNA ligation of ultramicrovolume using a EWOD microfluidic system," J. of Micromechanics and Microengineering, 18(4):45017 (7 pages), (2008).
Metzker, M. "Emerging Technologies in DNA Sequencing. Genome Research" 15 :1767 (2005).
Metzker, M., et al., "Termination of DNA synthesis by novel 3'-modifieddeoxyribonucleoside 5'-triphosphates," NAR, 22(20):4259-4267, (1994).
Moffitt et. al. "Recent Advances in Optical Tweezers". Annual Review of Biochemistry 77 :205 (Feb. 2008).
Neuman et. al. "Optical Trapping". Review of Scientific Instruments 75(9) : 2787 (2004).
Pon., R. "Solid-phase supports for oligonucleotide synthesis," Methods Mol. Biol., 20:465-496, (1993).
Randegger et. al., Real-time PCR and Melting curve analysis for reliable and rapid detection of SHV extended-Spectrum beta-lactamases. Antimicrobial Agents and Chemotherapy 45 (6) : 1730 (2001).
Richmond, K. E., et al., "Amplification and assembly of chip-eluted DNA (AACED): a method for high-throughput gene synthesis", Nucleic Acids Research, Oxford University Press, Surrey, GB, vol. 32, No. 17, pp. 5011-5018, Jan. 1, 2004.
Schaerli, Y., et al., "Continuous-Flow polymerase Chain reaction of single-copy DNA Micorfluidic Microdroplets," Anal. Chem., 81: 302-306, (2009).
Seo, T., et al., "Four-color DNA sequencing by synthesis on a chip using photocleavable fluorescent nucleotides," PNAS, 102(17):5926-5933, (Apr. 26, 2005).
Shabarova, Z., et al., "Chemical ligation of DNA: the first non-enzymatic assembly of a biologically active gene," Nucl. Acids Res., 19(15):4247-4251, (1991).
Stemmer et al. "Single-step assembly of a gene and entire plasmid from large numbers of oligodeoxyribonucleotides" Gene 164: 49 (1995).
Teh, S-Y, el al., "Droplet microfluidics," Lab on Chip, 8(2), (2008).
Tian, J., et al., "Accurate multiplex gene synthesis from programmable DNA microchips," Nature, 432 (7020):1050-1054, (Dec. 23-30, 2004).
Venkatesan, H. and Greenberg, M.,"Improved Utility of Photolabile Solid Phase Synthesis Supports for the Synthesis of Oligonucleotides Containing 3'-Hydroxyl Termini," J. of Org. Chem., 61:525-529, (Jan. 26, 1996).
Verma, S. and Eckstein, F., "Modified Oligonucleotides: Synthesis and Strategy for Users," Annu. Rev. Biochem., 67:99-134, (1998).
Xiong et al. "PCR based accurate synthesis of long DNA sequences" Nature protocols 1 (2): 791 (2006).
Xu, Y. and Kool, E., "A Novel 5'-Iodonucleoside allows efficient nonenzymatic ligation of single-stranded and duplex DNAs" Tetrahedron Letter, 38(32):5595-5598, (Aug. 11, 1997).
Xu, Y. and Kool, E., "High sequence fidelity in a non-enzymatic DNA autoligation reaction" Nuc. Acids Res., 27(3):875-881, (1999).
Xu, Y., et al., "Nonenzymatic autoligation in direct three-color detection of RNA and DNA point mutations" Nature Biotech., 19:148-52, (Feb. 2001).
Zhang, C., et al., "PCR microfluidic devices for DNA amplification," Biotechnology Advances, 24(3):243-284, 2006.
Zhou, X., et al. "Microfluidic PicoArray synthesis of oligodeoxynucleotides and simultaneous assembling of multiple DNA sequences", Nucleic Acids Research, vol. 32, No. 18, pp. 5409-5417, (2004).

\* cited by examiner

FIG. 3

METHODS FOR PREPARATIVE IN VITRO CLONING

RELATED APPLICATIONS

This application claims the benefit of U.S. provisional application Ser. No. 61/497,506, filed Jun. 15, 2011, the entire content of which is hereby incorporated by reference.

STATEMENT REGARDING FEDERALLY SPONSORED RESEARCH

This invention was made with United States Government support under the cooperative agreement number 70NANB7H7034N awarded by the National Institute of Standards and Technology. The United States Government has certain rights in the invention.

FIELD OF THE INVENTION

Methods are provided herein relate to the selection of a target nucleic acid sequence from a population of nucleic acid sequences. More particularly methods are provided for isolation of target sequences nucleic acid sequences of interest away from a library of nucleic acid sequences.

BACKGROUND

Methods for cloning nucleic acids and separating target sequences away from closely related but non-target sequences have been staple molecular biology tools. These common methods typically involve incorporation of the mixture of sequences with prepared vector pieces to prepare plasmids. The plasmids are then introduced into bacterial cells (transformation), which typically confer an antibiotic resistance to the strain. Selection of cells of the strain and proper dilution of the cells onto agar plates allows for identification of colonies arising from individual bacterial cells carrying individual sequences from the initial mixture. Subsequent manipulation of these colonies allow for the identification of target sequences away from the non-target sequences in the pool.

These common methods have drawbacks. The process is slow, with transformation of a bacterial strain and subsequent colony growth typically taking place overnight. Each colony must then be individually isolated and either grown in liquid media. Another drawback is that the transformation is relatively expensive.

The limiting dilution technique has been used to isolate single cells from a pooled suspension of cells, as well as for counting of DNA molecules. The basic method involves making a measurement of the number of cells or the concentration of DNA, diluting to very low concentration, and aliquoting into separate wells such that the number of cells or DNA molecules is less than one per well. Subsequent cell division or DNA amplification (e.g. by PCR) should reveal a Poissonian distribution of the wells corresponding to wells which were initially empty, seeded with one cell or molecule, and those seeded with multiples.

SUMMARY

Aspects of the invention relate to the isolation of target nucleic acid molecules having a predefined sequence. In some embodiments, the method comprises the steps of providing a population of nucleic acid molecules comprising a plurality of distinct nucleic acid molecules; providing a plurality of oligonucleotide tags; attaching the oligonucleotide tags to one end terminus of the plurality nucleic acid molecules thereby generating a subpopulation of nucleic acid-oligonucleotide tag molecules; amplifying the plurality of nucleic acid-oligonucleotide tag molecules using primers complementary to the plurality of oligonucleotide tags; and isolating at least one target nucleic acid-oligonucleotide tag molecule of the subpopulation of nucleic acid-oligonucleotide tag molecules.

In some embodiments, the method further comprises sequencing the at least one isolated target nucleic acid-oligonucleotide tag molecule and identifying the target nucleic acid. In some embodiments, the sequencing step is by high throughput sequencing. In some embodiments, the method further comprises amplifying the at least one target nucleic acid-oligonucleotide tag molecule.

In some embodiments, the step of isolating is by limiting dilution. In some embodiments, the target nucleic acid-oligonucleotide tag molecule is amplified.

Some aspects of the invention relate to a method of isolating a target nucleic acid, comprising (a) providing a population comprising a plurality of different nucleic acid molecules; (b) providing a plurality of microparticles, wherein each microparticle has an oligonucleotide sequence complementary to a portion of the nucleic acid molecules immobilized on its surface; (c) forming a population of nucleic acid molecules hybridized to the complementary oligonucleotide sequence on the microparticles; and (d) isolating at least one target nucleic acid molecule. In some embodiments, each microparticle has a single complementary sequence on its surface. In some embodiments, the complementary oligonucleotide sequences are identical. Yet in other embodiments, the complementary oligonucleotide sequences are different. In some embodiments, the plurality of nucleic acid molecules comprises an oligonucleotide tag at one terminus. In some embodiments, the plurality of nucleic acid molecules can have the same oligonucleotide tag or a different oligonucleotide tag. In some embodiments, the step of isolating is by limiting dilution. In some embodiments, the method further comprises amplifying the at least one target molecule.

Some aspects of the invention relate to a method of isolating a target nucleic acid, the method comprising (a) providing a population comprising a plurality of different nucleic acid molecules; (b) providing a dilution of the population of nucleic acid molecules; (c) separating the nucleic acid molecules into samples comprising a single molecule or a smaller number of molecules; (d) amplifying the single molecules thereby forming amplified nucleic acid molecules; (e) optionally repeating step (c) and (d) in samples that do not comprise a nucleic acid molecule; and (f) isolating at least one target nucleic acid molecule. In some embodiments, the target nucleic acid molecule has a predefined sequence. In some embodiments, the method further comprises sequencing the at least one target nucleic acid molecule.

DETAILED DESCRIPTION OF THE INVENTION

Aspects of the invention relate to methods and compositions for analyzing and separating at least one nucleic acid having a predefined sequence from a pool comprising a plurality of different nucleic acid sequences. In some aspects of the invention, the pool of nucleic acid sequences comprises variants of the nucleic acid sequence of interest and/or nucleic acid sequences having a similar length than the nucleic acid sequence of interest. Aspects of the invention is particularly useful for isolating nucleic acids sequence of interest from a population of nucleic acid sequences such as a library of nucleic acid sequences.

Aspects of the technology provided herein are useful for increasing the accuracy, yield, throughput, and/or cost efficiency of nucleic acid synthesis and assembly reactions. In some embodiments, the methods disclosed herein are particularly useful for isolating nucleic acid sequences for assembly of nucleic acid molecules having a predefined sequence. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predetermined sequence" or "predefined sequence" are used interchangeably and means that the sequence of the polymer is known and chosen before synthesis or assembly of the polymer. In particular, aspects of the invention is described herein primarily with regard to the preparation of nucleic acids molecules, the sequence of the oligonucleotide or polynucleotide being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotides constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different lengths. In some embodiments, the sequence of the polynucleotide construct may be divided up into a plurality of shorter sequences that can be synthesized in parallel and assembled into a single or a plurality of desired polynucleotide constructs using the methods described herein. In some embodiments, the assembly procedure may include several parallel and/or sequential reaction steps in which a plurality of different nucleic acids or oligonucleotides are synthesized or immobilized, primer-extended, and are combined in order to be assembled (e.g., by extension or ligation as described herein) to generate a longer nucleic acid product to be used for further assembly, cloning, or other applications.

In some embodiments, the nucleic acids molecules prepared according to the methods disclosed herein can be used for nucleic acid assembly and for assembly of libraries containing nucleic acids having predetermined sequence variations. Assembly strategies provided herein can be used to generate very large libraries representative of many different nucleic acid sequences of interest. In some embodiments, libraries of nucleic acids are libraries of sequence variants. Sequence variants may be variants of a single naturally-occurring protein encoding sequence. However, in some embodiments, sequence variants may be variants of a plurality of different protein-encoding sequences. Accordingly, one aspect of the technology provided herein relates to the assembling of precise high-density nucleic acid libraries. Aspects of the technology provided herein also provide precise high-density nucleic acid libraries. A high-density nucleic acid library may include more that 100 different sequence variants (e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, about 91%, about 92%, about 93%, about 94%, about 95%, about 96%, about 97%, about 98%, about 99%, or more of the sequences are predetermined sequences of interest).

In some embodiments, the methods and devices provided herein use oligonucleotides that are immobilized on a surface or substrate (e.g., support-bound oligonucleotides). Support-bound oligonucleotides comprise for example, oligonucleotides complementary to construction oligonucleotides, anchor oligonucleotides and/or spacer oligonucleotides. As used herein the term "support", "substrate" and "surface" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic. The support can include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein the term "array" refers to an arrangement of discrete features for storing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. The array may comprise interfeatures regions. Interfeatures will typically not carry any oligonucleotide on their surface and will correspond to inert space.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods, etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261. Additional methods applicable to synthesis of oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized or immobilized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and redistributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

In one aspect, the invention relates to a method for producing target polynucleotides having a predefined sequence on a solid support. In some embodiments, the synthetic polynucleotides can be at least about 1, 2, 3, 4, 5, 8, 10, 15, 20, 25, 30, 40, 50, 75, or 100 kilobases (kb), or 1 megabase (mb), or longer.

In some aspects, the invention relate to a method for the production of high fidelity polynucleotides. In exemplary embodiments, a composition of synthetic polynucleotides contains at least about 1%, 2%, 3%, 4%, 5%, 6%, 7%, 8%, 9%, 10%, 15%, 20%, 25%, 50%, 60%, 70%, 80%, 90%, 95% or more, copies that are error free (e.g., having a sequence that does not deviate from a predetermined sequence). The percent of error free copies is based on the number of error free copies in the composition as compared to the total number of copies of the polynucleotide in the composition that were intended to have the correct, e.g., predefined or predetermined, sequence.

Some aspects the invention relate to the preparation of oligonucleotides for high fidelity polynucleotide assembly. Aspects of the invention may be useful to increase the throughput rate of a nucleic acid assembly procedure and/or reduce the number of steps or amounts of reagent used to generate a correctly assembled nucleic acid. In certain embodiments, aspects of the invention may be useful in the context of automated nucleic acid assembly to reduce the time, number of steps, amount of reagents, and other factors required for the assembly of each correct nucleic acid. Accordingly, these and other aspects of the invention may be useful to reduce the cost and time of one or more nucleic acid assembly procedures.

It should be appreciated that the sequence of a nucleic acid (or library of nucleic acids or assembled nucleic acids) may include some errors that may result from sequence errors introduced during the oligonucleotides synthesis, the synthesis of nucleic acids, and/or from assembly errors during the assembly reaction. In some embodiments, unwanted sequences may be present in some nucleic acids. For example, between 0% and 50% (e.g., less than 45%, less than 40%, less than 35%, less than 30%, less than 25%, less than 20%, less than 15%, less than 10%, less than 5% or less than 1%) of the sequences in a library may be unwanted sequences. In some embodiments, nucleic acid having the predefined (or correct sequence) can be selectively isolated. The term "selective isolation", as used, herein, can involve physical isolation of a desired polynucleotide from others as by selective physical movement of the desired polynucleotide as well as selective inactivation, destruction, release, or removal of other polynucleotides than the polynucleotide of interest.

Devices and methods to selectively isolate the correct nucleic acid sequence from the incorrect nucleic acid sequences form a pool of nucleic acid sequences are provided herein. The correct sequence may be isolated by selectively isolating the correct sequence from the other incorrect sequences as by selectively isolating, moving or transferring the desired correct nucleic acid sequence. Alternatively, polynucleotides having an incorrect sequence can be selectively removed.

According to some methods of the invention, the nucleic acid sequences (construction oligonucleotides, assembly intermediates or desired assembled target nucleic acid) may first be diluted in order to obtain a clonal population of target polynucleotides (i.e. a population containing a single target polynucleotide sequence). As used herein, a "clonal nucleic acid" or "clonal population" or "clonal polynucleotide" are used interchangeably and refer to a clonal molecular population of nucleic acids, i.e. to nucleic acids or polynucleotide that are substantially or completely identical to each other. Accordingly, the dilution based protocol provides a population of nucleic acid molecules being substantially identical or identical to each other. In some embodiments, the polynucleotides are diluted serially. In some embodiments, the device integrates a serial dilution function. In some embodiments, the assembly product is serially diluted to produce a clonal population of nucleic acids. In some embodiments, the concentration and the number of molecules can be assessed prior to the dilution step and a dilution ratio is calculated in order to produce a clonal population. In an exemplary embodiment, the assembly product is diluted by a factor of at least 2, at least 3, at least 4, at least 5, at least 6, at least 7, at least 10, at least 20, at least 50, at least 100, at least 1,000 etc. . . . . .

One of skill in the art will appreciate that the traditional limiting dilution techniques which follows the statistical Poisson distribution is often time consuming. As determined by the Poisson distribution, limiting dilution should result in a single-hit e.g. one clone per well. However, if the sample is very large, a variable number of clones (e.g. two-hit) can be present in a single well and multiple rounds are required in order to assure monoclonality. Aspects of the invention relate to methods for preparative isolation of nucleic acid molecules in a more efficient way than the method of limiting dilution.

In some aspects of the invention, the nucleic acid sequences are sorted by an improved limiting dilution technique. Specifically, in some embodiments, the methods use a feedback loop to increase the efficiency of separation beyond the Poisson distribution of limiting dilution. In some embodiments, the process disclosed herein is an iterative process. The process can use a fluorescence signal as a feedback mechanism for identification of empty samples, thereby allowing for more effective in vitro cloning than the Poisson limiting dilution.

Figure 1:
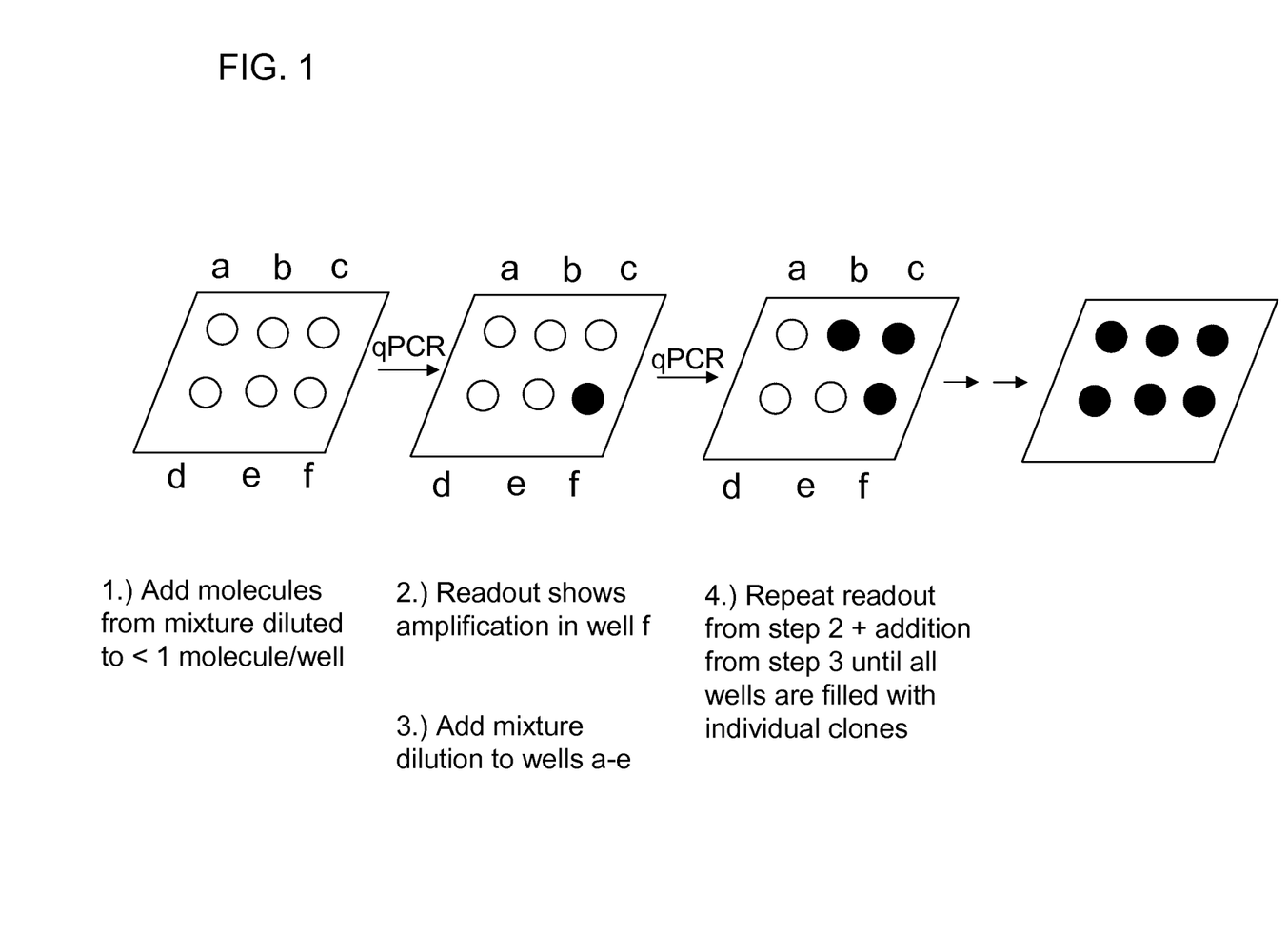
FIG. 1 illustrates a non-limiting exemplary method of in vitro cloning by increasing the limiting dilution.

In some embodiments, a pool of nucleic acid sequences is diluted to form a diluted solution or mixture of nucleic acid molecules. The nucleic acid molecules are separated into samples comprising a single or a smaller number of molecules. For example, the diluted solution can be used for seeding the wells of a plate such that individual wells of a plate (e.g. 96 well plate) are filled with less than one molecule per well. Cycles of quantitative PCR (qPCR) reactions can be run on all the samples, allowing for identification of samples (e.g. wells) initially seeded with individual molecules. Presence of nucleic acid sequences within each sample can be determined by fluorescence. Because of the way the initial dilution is set, very few samples (e.g. well) would be initially seeded with multiple molecules. As illustrated in FIG. 1, step 1, readout of the fluorescence shows the presence of amplification products in a small number of wells (well f, FIG. 1, step 1). Sample seeded which did not contain any nucleic acid molecules (wells a-e, FIG. 1) can then be supplemented with the dilution solution (step 3, FIG. 1) and quantitative PCR can be performed again. As illustrated in FIG. 1, step 4, readout of the fluorescence shows the presence of amplification products in an increasing number of wells (well b, c and f). The process can be repeated until substantially all the samples or wells contain an amplified population of nucleic acid molecules.

In some aspects of the invention, specific hybridization can be used as a method for identifying and/or retrieving nucleic acids of interest. In some aspects of the invention, solid supports, such as microparticles or beads, having a single ligand site for attachment of nucleic acid can be used to retrieve a single nucleic acid molecule. The single ligand site can be an oligonucleotide sequence complementary to part of the sequence of the nucleic acid sequences to be analyzed or complementary to an oligonucleotide tag attached to the nucleic acid sequences. Each nucleic acid of the plurality of nucleic acid sequence can be tagged with a different oligonucleotide tag or with the same oligonucleotide tag. For example, the nucleic acid sequences of the plurality of nucleic acid sequences can be ligated to a single oligonucleotide tag. Yet in other embodiments, a plurality oligonucleotide tags are provided. In some embodiments, each oligonucleotide tag has the same length. In some embodiments, the length of the oligonucleotide tag is at least 4 nucleotides long, at least 20 nucleotides long, at least 20 nucleotides long, at least 30 nucleotides long, or at least 40 nucleotides long.

In some embodiments, solid supports having complementary sequences immobilized thereon are provided. Complementary sequences may be sequences complementary to the oligonucleotide tag sequence or sequences complementary to a portion of the plurality of nucleic acid sequences. Oligonucleotide sequences may be covalently or non-covalently linked to the surface of the solid support. In some embodiments, the solid support may be a bead, microparticle, plate, membrane, array and the like. In preferred embodiments, the solid support is a microparticle or a bead. Typically the size range of the bead range from 1 µm to 1000 µm diameter. The size of the beads may be chosen to facilitate the manipulation of the beads. In some embodiments, the complementary sequences are attached to the solid support. Yet in other embodiments, the sequences complementary to the oligonucleotide tags are synthesized on the solid support as disclosed herein. In some embodiments, the solid support is made of controlled pore glass, nucleoside-derivatized CPG, cellulose, nylon, acrylic copolymers, dextran, polystyrene, magnetic beads and the like. In some embodiments, the solid support is porous. Typically, the beads have a pore size ranging from 500 to 1000 angstrom. Yet in other embodiments, the solid support is non porous.

Figure 2:
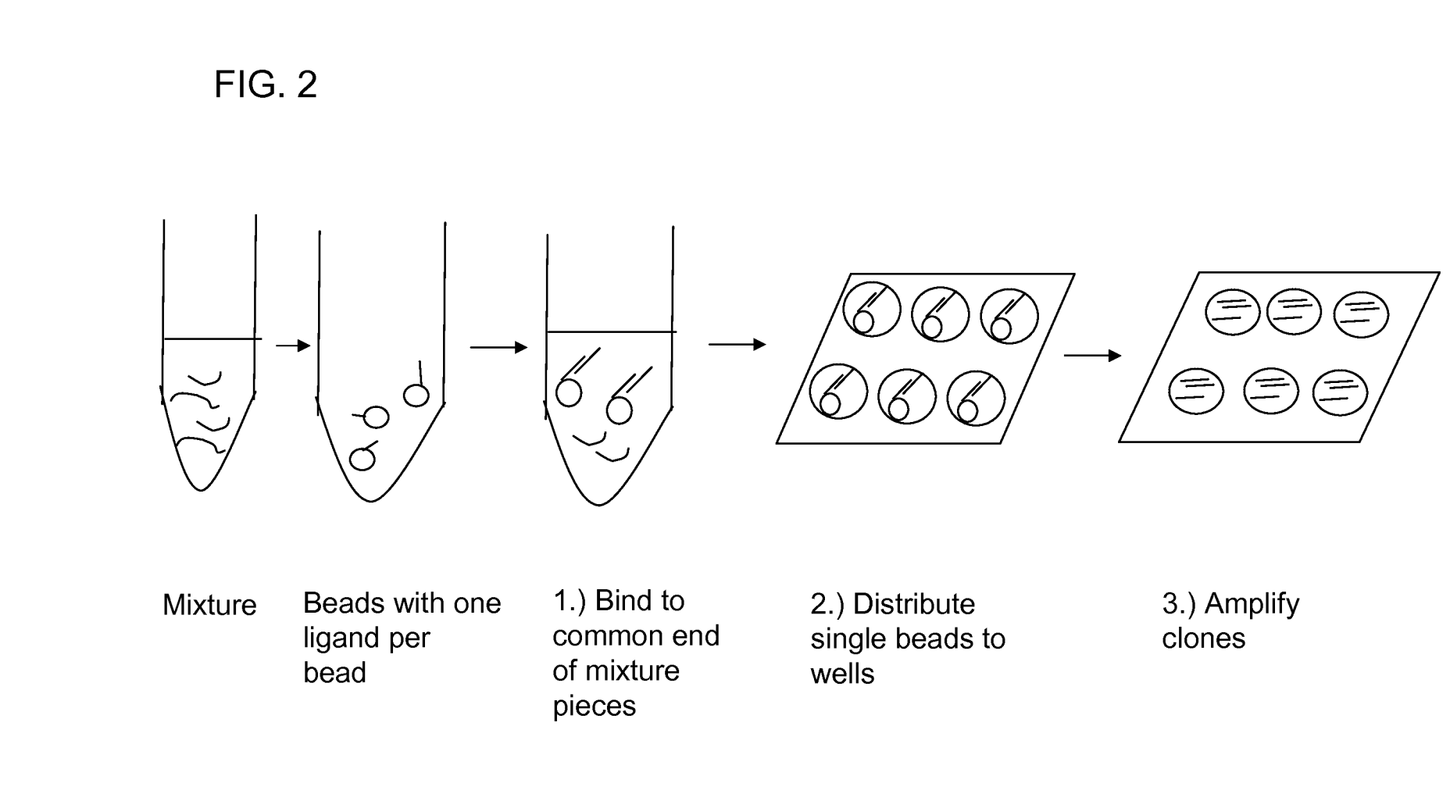
FIG. 2 illustrates a non-limiting exemplary method of in vitro cloning using beads with single ligand sites for nucleic acid attachment.

In preferred embodiments, a population of beads each bead having thereon a single complementary sequence to the oligonucleotide tag can be used such as each bead of the population is capable of retrieving a single nucleic acid molecule. As illustrated in FIG. 2 (step 1), the nucleic acid molecules are mixed with beads comprising the single ligand site (e.g. single complementary sequence) under conditions favorable for the hybridization complementary sequences. The plurality of beads having nucleic acid sequences attached thereon may be suspended and separated into samples (e.g. in wells of a microtiter plate, FIG. 2, step 2). In some embodiments, the beads may be subjected to limited dilution or to the methods disclosed herein and distributed and separated such as each well contains a single bead. Nucleic acid sequences immobilized onto the isolated beads may be subjected to amplification using primers.

In some embodiments, the target polynucleotides are amplified after obtaining clonal populations. In some embodiments, the target polynucleotide may comprise universal (common to all oligonucleotides), semi-universal (common to at least a portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, a target nucleic acid molecule contains both universal and unique amplification sequences, which can optionally be used sequentially.

In some embodiments, primers/primer binding sites may be designed to be temporary. For example, temporary primers may be removed by chemical, light based or enzymatic cleavage. For example, primers/primer binding sites may be designed to include a restriction endonuclease cleavage site. In an exemplary embodiment, a primer/primer binding site contains a binding and/or cleavage site for a type IIs restriction endonuclease. In such case, amplification sequences may be designed so that once a desired set of oligonucleotides is amplified to a sufficient amount, it can then be cleaved by the use of an appropriate type IIs restriction enzyme that recognizes an internal type IIs restriction enzyme sequence of the oligonucleotide. In some embodiments, after amplification, the pool of nucleic acids may be contacted with one or more endonucleases to produce double-stranded breaks thereby removing the primers/primer binding sites. In certain embodiments, the forward and reverse primers may be removed by the same or different restriction endonucleases. Any type of restriction endonuclease may be used to remove the primers/primer binding sites from nucleic acid sequences. A wide variety of restriction endonucleases having specific binding and/or cleavage sites are commercially available, for example, from New England Biolabs (Beverly, Mass.).

In certain exemplary embodiments, a detectable label can be used to detect one or more nucleotides and/or oligonucleotides described herein. In some embodiments, detectable label is used to detect amplified molecules, for example, after quantitative PCR. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorimidases, phosphatases, peroxidases, cholinesterases and the like. Identifiable markers also include radioactive compounds such as 125I, 35S, 14C, or 3H. Identifiable markers are commercially available from a variety of sources. Preferably the oligonucleotide probes or nucleotides are fluorescently labeled with four different fluorophores, each fluorophore being associated to a particular base or nucleotide.

In some aspects of the invention, the sequence of one or more nucleic acid molecules is determined and/or the nucleic acid molecules having the correct sequences of interest are selectively isolated. This can typically accomplished by conventional or next generation primary sequencing. In some embodiments, methods to sequence verify nucleic acid sequences using high throughput sequencing are provided. In some embodiments, nucleic acid molecules are sequenced by synthesis. Sequence determinations can be made by any available method permitting the querying of the sequence of an individual molecule ("single molecule sequencing"), whether directly or through the querying of an amplified population of nucleic acids derived from a single molecule ("polony sequencing"). The method of sequence determination can be non-destructive, to the extent that the objective of the sequence determination is the identification of a subsequently useful oligonucleotide. Methods of polymerase amplification and sequencing are described, for example, in U.S. Patent Application Nos. 2005-0079510 and 2006-0040297; in Mitra et al., (2003) Analytical Biochemistry 320: 55-65; Shendure et al., (2005) Science 309:1728-1732; and in Margulies et al., (2005) Nature 437:376-380, the complete disclosures of each of which are herein incorporated by reference. As discussed in Shendure et al. (2005) Science 309:1729, polony amplification can involve, for example, in situ polonies, in situ rolling circle amplification, bridge PCR, picotiter PCR, or emulsion PCR. Generally, an oligonucleotide to be amplified is prepared to include primer binding sites, whether as part of its sequence when initially synthesized or by subsequent ligation to adaptor molecules bearing the primer binding sites. In some embodiments, prior to sequencing, the oligonucleotides are immobilized at distinct locations (e.g., predetermined, addressable locations or random locations) on a solid support. In the Genome Sequencer 20 System from 454 Life Sciences, for example, beads from polony amplification are deposited into wells of a fiber-optic slide. In the method of Shendure, beads from polony amplification are poured in a 5% acrylamide gel onto a glass coverslip manipulated to form a circular gel approximately 30 microns thick, giving a disordered monolayer.

Figure 3:
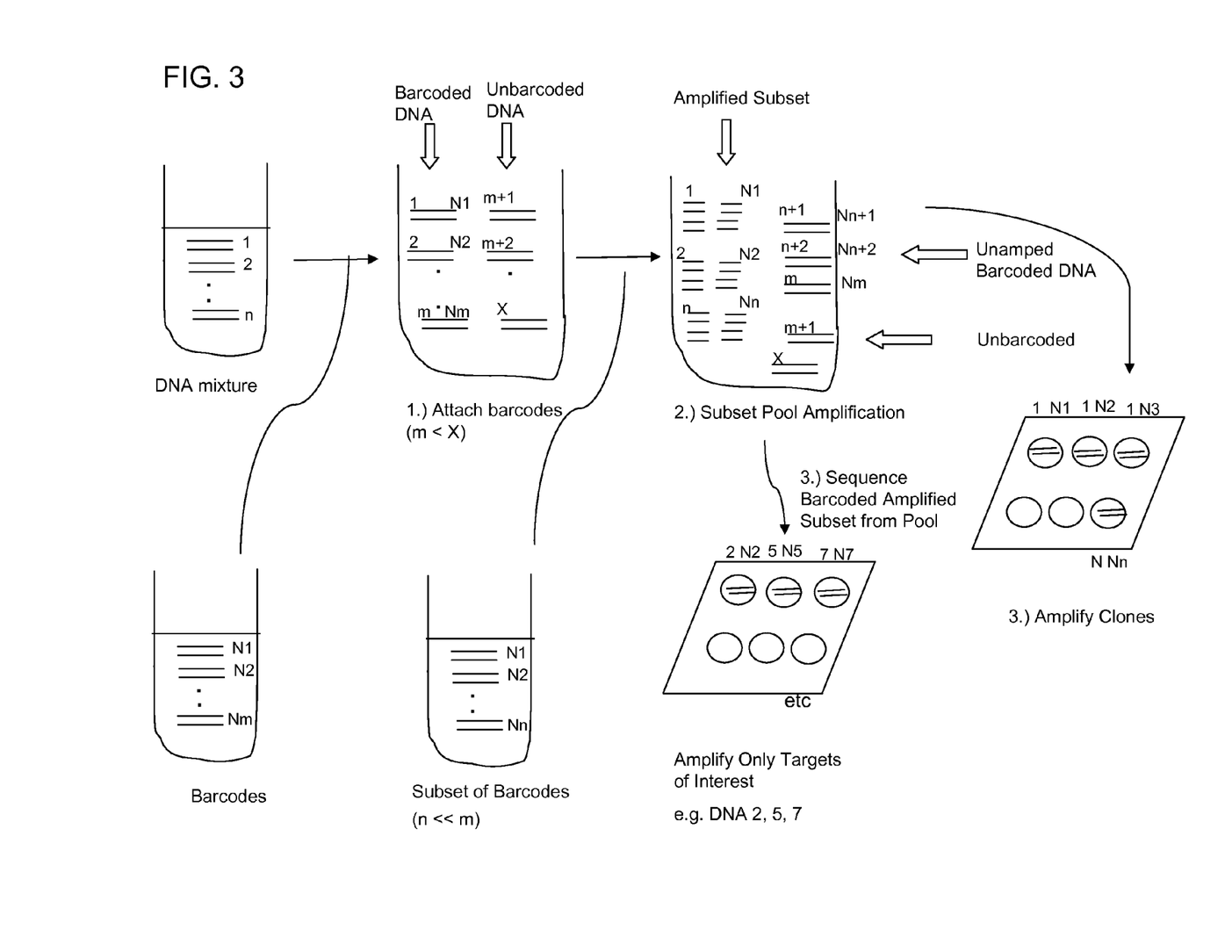
FIG. 3 illustrates a non-limiting exemplary method of in vitro cloning using a library of barcode sequences.

In some aspects of the invention, the methods involve the use of a library of identifying oligonucleotide tags (also referred herein as barcodes). In some embodiments, the length of the oligonucleotide tags may vary depending on the size of complexity of the nucleic acid population to be analyzed. In general, a longer oligonucleotide sequence tag will allow for a larger population of oligonucleotide tags. In some embodiments, each barcode differs from the other by at least 2 nucleotides. In preferred embodiments, a portion of the library of oligonucleotide tags is used and attached to one end terminus of the plurality of nucleic acid sequences in the population (or pool) in a stoichiometry such that a small sampling (i.e. subpopulation) of the plurality of nucleic acids in the population is bar-coded. For example, and as illustrated in FIG. 3, the nucleic acid population may contain X nucleic acid molecules and a plurality m of nucleic acid tags can be provided wherein m inferior to X. After attachment of the oligonucleotide tags to the nucleic acid molecules, the resulting sub-population will comprise m bar-coded nucleic acid molecules, the remaining nucleic acid molecules being free of oligonucleotide tags ("unbarcoded"). In some embodiments, a number of primers n specific to a known set n of specific barcode sequences can be added, wherein n is inferior to m. Addition of primers specific to the oligonucleotide tags or barcode under favorable conditions results in the hybridization of the primers to their specific biding sites and allows for specific amplification of a subset n of the bar-coded nucleic acid sequences.

In some embodiments, the barcode or oligonucleotide tags are attached to the end terminus of a sub-population population of nucleic acid sequences thereby forming nucleic acid sequences-oligonucleotide tag conjugates. For example, the barcode or oligonucleotide tag can be attached using TA cloning technique. This technique relies on the ability of adenine (A) and thymine (T) on different nucleic acid sequences (e.g. oligonucleotide tag sequences and nucleic acid sequences of interest) to hybridize and ligate together in presence of ligase. In some embodiments, the oligonucleotide tag sequences or the nucleic acid sequences to be analyzed are amplified using a Taq polymerase which preferentially adds a A at the 3' end. In some embodiments, the sequences comprising a A at the 3' end are hybridized and ligated to sequences comprising a T at the 5' end.

Because of the size of the library of barcodes, each barcode sequence is expected to appear only once in the subpopulation, thus ensuring clonality. The bar-coded subpopulation may then be amplified using primers for a known set of specific barcode sequences (i.e. a subset pool), which represents a desired sampling (or subset) of the subpopulation of nucleic acids.

At this point, this amplified subset population may then be separated into samples (e.g. aliquoted into wells) and amplified. In some embodiments, primers specific to the individual barcode sequence can be used to preparatively clone an individual molecule from the original population of nucleic acid molecules. One skilled in the art would appreciate that the efficiency of the direct cloning methods disclosed herein may be limited by Poisson statistics due to the balance of the probability of any specific barcode appearing exactly once as a ligated product to a nucleic acid molecule from the mixture. To increase the efficiency well above Poisson statistics, other manipulations may be performed, for example sequencing the amplified subset population. Because the attached barcode can be used for multiplex sequencing on a high throughput next generation sequencing, the sequences of each nucleic acid molecule from the mixture as well as its attached barcode can be determined. The sequencing data may then be used to determine target molecules of interest from the mixture, as well as the identity of which barcodes they are attached to in the subset pool. These target molecules may then selectively amplified from the subset pool in individual wells, clonally separating them from non-target sequences in the mixture.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to International application No PCT/US2009/055267 filed Aug. 27, 2009, PCT/US2010/057405 filed Nov. 25, 2010, PCT/US 2010/057392 filed Nov. 19, 2010, PCT/US2010/055298, filed Nov. 3, 2010, PCT/US 2011/020335 filed Jan. 6, 2011, PCT/US2011/36433, filed May 13, 2011, U.S. provisional application 61/412,937. filed Nov. 12, 2010, to U.S. provisional application 61/418,095 filed Nov. 30, 2010 and U.S. provisional application 61/466, 814. filed Mar. 23, 2011, entitled "Methods and Devices for Nucleic Acids Synthesis". All publications, patents and sequence database entries mentioned herein are hereby incorporated by reference in their entirety as if each individual publication or patent was specifically and individually indicated to be incorporated by reference.

What is claimed is:

1. A method of isolating a target nucleic acid molecule, the method comprising:
    (a) providing a plurality of nucleic acid molecules;
    (b) providing a library of oligonucleotide tags, each oligonucleotide tag comprising a region having a different sequence than the other tags in the library and comprising a primer binding site;
    (c) ligating at least a subset of the plurality of nucleic acid molecules with the library of oligonucleotide tags, thereby generating a population of conjugates, wherein each conjugate has a unique oligonucleotide tag that is different in sequence than that of the other conjugates;
    (d) amplifying in a pool at least a subset of the population of conjugates using one or more primers each having sequence complementarity to the primer binding site thereon;
    (e) isolating at least one conjugate of the amplified conjugates from the pool, wherein the isolated conjugate comprises a target nucleic acid molecule having a predetermined sequence; and
    (f) removing the oligonucleotide tag attached thereto to recover the target nucleic acid molecule.

2. The method of claim 1 further comprising sequencing the amplified conjugates.

3. The method of claim 2 wherein the sequencing step comprises high throughput sequencing.

4. The method of claim 2 wherein the step of isolating comprises clonally separating the target nucleic acid molecule from non-target by selectively amplifying, after the sequencing step, at least one conjugates.

5. The method of claim 1 wherein the step of isolating comprises limiting dilution.

6. The method of claim 5 further comprising amplifying the isolated conjugate.

7. A method of isolating a target nucleic acid molecule, the method comprising:
    (a) providing a population of nucleic acid molecules having different predetermined sequences;
    (b) providing a plurality of oligonucleotide sequences that are different from one another in sequence and are immobilized on microparticles, each microparticle having a single copy of oligonucleotide sequence immobilized on its surface, wherein each single copy of oligonucleotide sequence is uniquely complementary to a corresponding nucleic acid molecule of the population;
    (c) hybridizing the population of nucleic acid molecules to the plurality of oligonucleotide sequences, thereby forming a population of hybridized microparticles, each hybridized microparticle having a single nucleic acid molecule attached thereon via hybridization with its corresponding uniquely complementary oligonucleotide sequence;
    (d) separating the population of hybridized microparticles into samples, each sample comprising a single hybridized microparticle; and
    (e) isolating at least one hybridized microparticle comprising a target nucleic acid molecule having a predetermined sequence.

8. The method of claim 7 wherein each nucleic acid molecule comprises an oligonucleotide tag at one terminus.

9. The method of claim 8 wherein the plurality of nucleic acid molecules have the same oligonucleotide tag.

10. The method of claim 8 wherein the plurality of nucleic acid molecules have different oligonucleotide tags.

11. The method of claim 7 wherein the step of isolating comprises limiting dilution.

12. The method of claim 7 further comprising amplifying the target nucleic acid molecule.

13. The method of claim 1 wherein the step of amplifying comprises providing a plurality of primers in stoichiometry wherein the absolute number of primers is less than the absolute number of oligonucleotide tags.

14. The method of claim 1 wherein in the step of providing a library of oligonucleotide tags, each oligonucleotide tag in the library differs from one another by at least 2 nucleotides.

15. The method of claim 1 wherein step (d) is performed in solution.

16. The method of claim 1 wherein in step (b), the library of oligonucleotide tags is provided in stoichiometry wherein the absolute number of oligonucleotide tags is less than the absolute number of nucleic acid molecules.

17. The method of claim 1 further comprising isolating a plurality of target nucleic acid molecules having different predetermined sequences and assembling the plurality of target nucleic acid molecules.

18. The method of claim 1 wherein in step (a) the nucleic acid molecules are synthesized on a solid support.

19. A method of isolating a target nucleic acid molecule, the method comprising:

(a) providing a population of nucleic acid conjugates, each having a distinct predetermined sequence and a oligonucleotide tag that is different in sequence than that of the other conjugates, wherein each predetermined sequence and each oligonucleotide tag are conjugated via ligation;

(b) amplifying in a pool at least a subset of the population of nucleic acid conjugates using primers having sequence complementarity to the oligonucleotide tags conjugated thereto;

(c) isolating a target nucleic acid molecule having a predetermined sequence from the amplified nucleic acid molecules in the pool; and (d) removing the oligonucleotide tag conjugated thereto to recover the target nucleic acid molecule.

20. The method of claim 1, wherein the removing step (f) comprises contacting the isolated conjugate with an endonuclease to produce a double-stranded break.

21. The method of claim 20 further comprising isolating a plurality of target nucleic acid molecules having different predetermined sequences that together comprise and can be assembled into a target polynucleotide.

22. The method of claim 1, wherein the removing step (f) comprises selectively amplifying the target nucleic acid molecule.

23. The method of claim 19, wherein the removing step (d) comprises contacting the isolated target nucleic acid molecule with an endonuclease to produce a double-stranded break.

24. The method of claim 23 further comprising isolating a plurality of target nucleic acid molecules having different predetermined sequences that together comprise and can be assembled into a target polynucleotide.

25. The method of claim 19, wherein the removing step (d) comprises selectively amplifying the target nucleic acid molecule.

* * * * *

UNITED STATES PATENT AND TRADEMARK OFFICE
CERTIFICATE OF CORRECTION

PATENT NO. : 9,752,176 B2
APPLICATION NO. : 13/524164
DATED : September 5, 2017
INVENTOR(S) : Li-Yun A. Kung et al.

It is certified that error appears in the above-identified patent and that said Letters Patent is hereby corrected as shown below:

On the Title Page

In item (73), the Assignee should be amended as indicated below:

(73) Assignee: Gen9, Inc., Cambridge, MA (US)

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*